July 19, 1955
F. R. CODDINGTON
Plant Pat. 1,406
PEACH TREE
Filed Jan. 28, 1954
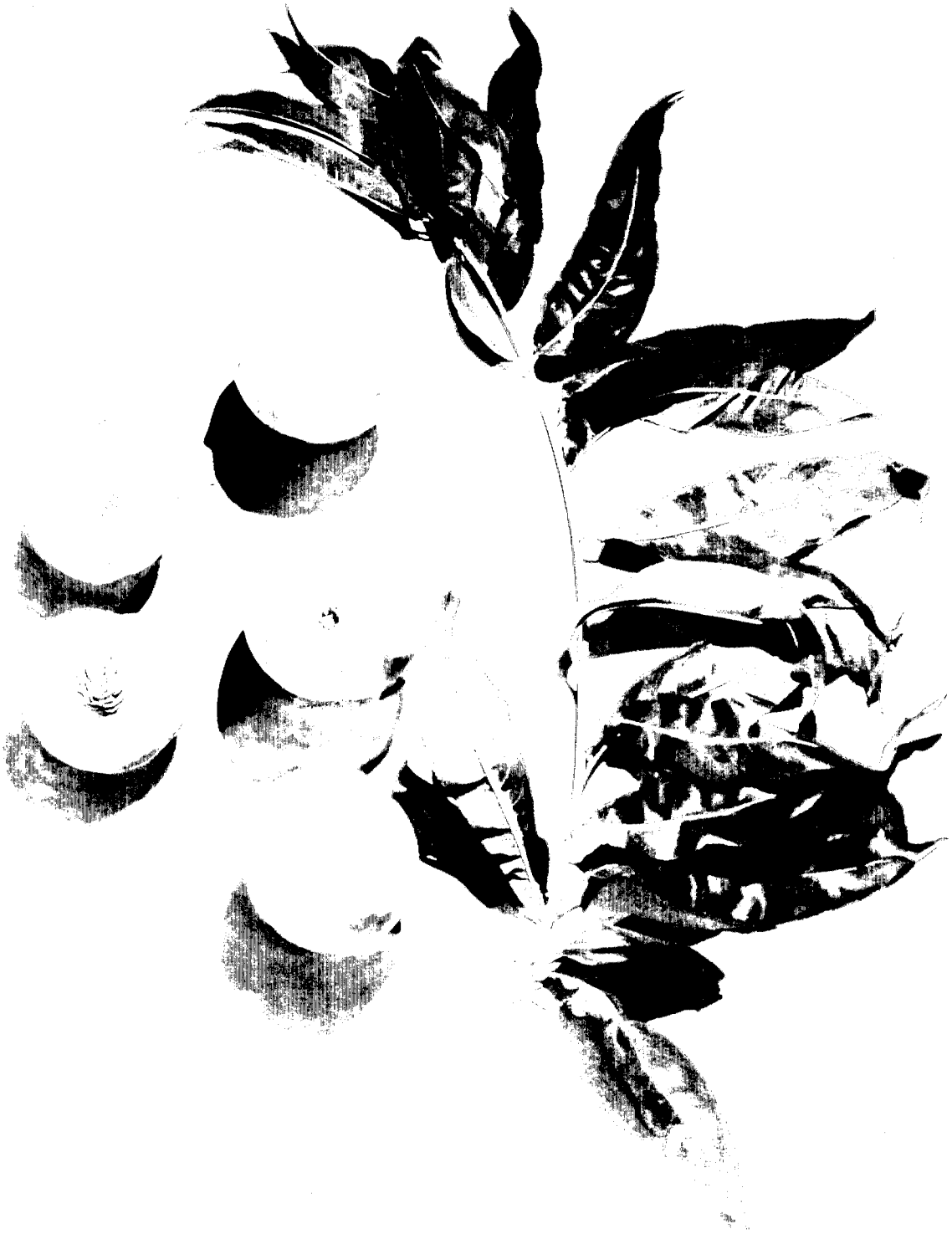
FRANK R. CODDINGTON
INVENTOR
HUEBNER, BEEHLER, WORREL & HERZIG
ATTORNEYS
BY Richard M. Worrel United States Patent Office Plant Pat. 1,406
Patented July 19, 1955

1,406

PEACH TREE

Frank R. Coddington, Parlier, Calif.

Application January 28, 1954, Serial No. 406,909

1 Claim. (Cl. 47—62)

The present discovery relates to an improved peach tree of the yellow-flesh freestone type and more particularly to such a peach tree of the Elberta family of peach trees.

Although the general characteristics of the new peach tree suggest in many ways, not including its ripening period, that it might be a cross between the J. H. Hale (unpatented) and the Burbank July Elberta of Plant Patent No. 15, it is known to be a bud sport of the latter. The applicant discovered the new variety while examining for packing and marketing the fruit of a July Elberta orchard near the city of Parlier in the county of Fresno of the State of California. This new variety discovered as a bud sport was unconditionally given to the applicant by the owner of the orchard. Being a graduate pomologist and nurseyman in addition to a commercial fruit buyer, he readily recognized the distinguishing characteristics of the new variety and subsequently, as soon as the wood of the new variety had reached the proper condition, budded twelve scions of the new variety into other host peach trees. This asexual reproduction was first accomplished in the applicant's orchard near the intersection of South Avenue and River Bend Avenue in said county of Fresno and all of the initial buds readily established themselves and flourished. The initial buds and others which have subsequently been made have proved the dependable characteristics of the new variety by accurate ingemination thereof.

Of the patented peaches, the subject variety is probably most similar in general characteristics to the Burbank peach tree of Plant Patent No. 15 but is distinguished therefrom by earlier ripening, somewhat lighter flesh, usually more uniform skin coloration and other characteristics which will soon be recognized.

The Smith peach tree of Plant Patent No. 803 is quite similar to the Burbank tree and thus is in many respects similar to the new variety. Among other features, however, the subject peach tree is distinguished from the Smith peach tree by its difference in ripening period.

Also, comparison with the Fulkerth peach tree of Plant Patent No. 1,172 and the Stribling peach tree of Plant Patent No. 1,144 discloses substantial similarity in several particulars, the new variety ripens approximately one month prior to the former and about a week later than the latter.

The drawing shows a characteristic branch from the new variety bearing the characteristically closely clustered leaves, three characteristic whole fruit variously positioned to disclose a maximum of the skin surface thereof, and a halved peach showing the flesh coloration, pit well, and a pit.

Further distinguishing features of the subject peach tree over known varieties will be noted in reference to the following description in which color designations are according to the "Dictionary of Color" by Maerz and Paul, Second Edition.

Tree: Medium large, vigorously stout branching with well-knit forks of divergent habit, hardy, very productive, and regular bearing.

*Trunk.*—Characteristic of Elberta family generally in size, surface characteristic, and color.

*Leaves.*—Length approximately 7 inches when mature, width 1⅝ inches, medium large, ovate at base, acutely pointed at tip, medium thick, rugose, and profuse. The leaves occur in relatively closely spaced relation along the small branches and occasionally occur in pairs or triads.

Color—Upper surface ranging from K–9 (Runnymeade) to J–10 (Amazon Green) of Plate XXIX, page 81. Lower surfaces: ranging from H–8 (approximately Jasper Green) to F–8 (approximately Gretna Green) of Plate XXIX, page 81. Veins: generally cream color varying from H–1 to G–2 of Plate IX, page 41.

Margin—Minutely serrated.

Petiole—Medium short and relatively thick.

Glands—Small and usually in pairs, varying from globose to reniform.

Flowers: Blossoms two or three days later than the July Elberta and has blossoms similar thereto but somewhat more pink in coloration.

Fruit: Maturity for eating approximately June 20 when grown under the ecological conditions encountered on the applicant's farm in said Fresno County, approximately one week earlier than the July Elberta.

*Size.*—Usually uniform, medium to large. Axial diameter approximately 3 inches, transverse diameter in suture plane approximately 2⅞ inches, and diameter at right angles to suture plane approximately 3 inches.

*Form.*—Usually symmetrical and globose but occasionally varying to asymmetrical. Most frequently substantially spherical with deep stem end cavity.

*Suture.*—Pronounced at stem end frequently extending nearly to pit, much shallower in progression from stem to apex and rapidly disappearing at apex.

*Stem cavity.*—Usually deep and symmetrically funnel shaped but occassionally slightly elongated in suture plane.

*Base.*—Well rounded.

*Apex.*—Short apical.

*Stem.*—Medium length, approximately ½ inch, medium caliber, and glaborous.

*Skin.*—Thin substantially uniform texture and color, pubescent and easily parted from flesh when fully ripe.

Color—At stem end substantially "Empire Yellow" of J–3 Plate IX, page 41 or E–1 of Plate X, page 43. Basic skin coloring where exposed to sunlight "Coral Blush" of F–10 Plate I, page 25. Splotches approximately "Flint Red" or "Meadowsweet" of K–9 Plate II, page 27 or K–8 Plate IV, page 31.

*Flesh.*—

Color—Light yellow ranging from E–1 to J–6 of Plate IX page 41 tending toward the lighter shades except where overripe or bruised where shade J–6 is reached. Minor streakings of "Carnival Red" or "Troubador Red" of L–7 or L–8 respectively of Plate III, page 28.

Texture—Medium firm until excessively ripened.

Fibers—Few and fine.

*Ripening characteristics*—Fairly evenly but earliest at apex.

Flavor—Pleasant and mild.

Aroma—Distinct.

Eating quality—Excellent.

*Stone.*—Free although minor quantities of flesh adherent to ventral side of pit when not fully ripe.

Fibers—Medium and relatively tender.

Size—Medium small. Length approximately 1½ inches, width approximately ⅞ inch, thickness approximately ⅝ to ¾ inch.

Form—Obovoid, cuneate toward base. Base: Oblique. Apex: Sharply acute. Sides: Substantially symmetrical. Surface: Irregularly furrowed medium to pronounced and pitted as general in Elberta family.

Color—Light brown varying from "Rose Glow" or "Longchamps" of D–9 or A–9 of Plate V, page 33 to "Tuscon Tan Sauterne" of C–8 Plate XIII, page 49.

Splitting tendency—None noticed in several years of observation.

Use: Fresh, dried, frozen and canned.

Keeping quality: Good.

Shipping quality: Expected to be satisfactory but not thoroughly tested.

Having thus described my discovery, I claim:

A new and distinct variety of peach tree, substantially as shown and described, characterized by marked similarity to the Burbank July Alberta of Plant Patent No. 15 of which it is a bud sport and from which it is distinguished by its blossoming a few dayes later, with bloom generally similar in appearance but of more pink coloration, its ripening approximately one week earlier, and its comparatively dense foliage, the leaves occasionally occurring in pairs and triads and the leaf buds being relatively closely spaced.

No references cited.